United States Patent

Chikami

[11] Patent Number: 5,897,312
[45] Date of Patent: Apr. 27, 1999

[54] BRACKET FOR CORRECTING DENTITION, METHOD FOR PRODUCING THE SAME, AND METHOD FOR IMPROVING ADHESIVITY OF POLYCARBONATE

[76] Inventor: Kunio Chikami, 211-1, Minamikuma, Kochi-shi, Kochi-ken, Japan

[21] Appl. No.: 08/825,154

[22] Filed: Mar. 26, 1997

Related U.S. Application Data

[62] Division of application No. 08/498,837, Jul. 6, 1995, Pat. No. 5,681,166.

[30] Foreign Application Priority Data

Dec. 5, 1994 [JP] Japan ................................ 6-300774

[51] Int. Cl.$^6$ ....................................................... A61C 3/00
[52] U.S. Cl. .................................................................. 433/9
[58] Field of Search ................................................ 433/9, 8

[56] References Cited

U.S. PATENT DOCUMENTS

| | | | |
|---|---|---|---|
| 4,266,053 | 5/1981 | Imanaka et al. | 544/196 |
| 4,348,456 | 9/1982 | Imanaka et al. | 428/336 |
| 5,001,008 | 3/1991 | Tokita et al. | 428/400 |
| 5,141,436 | 8/1992 | Orlowski et al. | 433/9 |
| 5,267,855 | 12/1993 | Tuneberg | 433/9 |
| 5,558,516 | 9/1996 | Horn et al. | 433/9 |

*Primary Examiner*—Nicholas D. Lucchesi
*Attorney, Agent, or Firm*—Armstrong, Westerman, Hattori, McLeland & Naughton

[57] ABSTRACT

An object of the present invention is to increase the adhesive strength of the polycarbonate bracket for correcting dentition.

The bracket for correcting dentition comprises a polycarbonate bracket, an adhesive layer being applied to the bottom surface of the bracket and subjected to an irradiation of a microwave and a plastically deformable photocuring resin layer being applied to the adhesive layer.

2 Claims, 1 Drawing Sheet

BRACKET FOR CORRECTING DENTITION, METHOD FOR PRODUCING THE SAME, AND METHOD FOR IMPROVING ADHESIVITY OF POLYCARBONATE

This is a divisional of application Ser. No. 08/498,837 filed Jul. 6, 1995 now U.S. Pat. No. 5,681,166.

BACKGROUND OF THE INVENTION

The present invention relates to a bracket for correcting dentition, which is made of polycarbonate, and further relates to a bracket for correcting dentition, of which adhesivity to a plastically deformable synthetic resin layer bonded to the bracket, is enhanced.

A bracket for correcting dentition is a device for correcting dentition by fitting and fixing it directly to a tooth in combination use of a wire.

Many of conventional brackets used for correcting dentition are those made of metals, but from a point that deformation occurs by a lengthy use and also from the viewpoint of their weight, synthetic resin brackets are replacing them. As the synthetic resins, polycarbonate is most suitable from a point that a high strength, staining resistance and high water resistance are required.

However, bonding of polycarbonate is difficult, and suitable non-toxic adhesives imparting a high adhesive strength are very few. Therefore necessary adhesive strength is furnished by physical methods, such as roughening of a bond surface of the bracket and fitting of a metal net to the bottom surface of the bracket (Japanese Patent Publication Kokai No. 2-265541).

Also the bracket is small (about 3 to about 4 mm square), so skill is required in fixing it and adjusting a position of it. In order to make it easy to set the position of the bracket and fix it, there was developed a method to bond a plastically deformable photocuring synthetic resin layer (also referred to as a base plate) to the bottom surface of the bracket through an adhesive layer interposed therebetween and fix the base plate to the tooth after or at the same time when the shape conforming to a direction and surface condition of the tooth is obtained (Japanese Patent Publication Kokai No. 5-269147).

Also in this bonding of the base plate and bracket, there still occurs the above-mentioned problem of the adhesion failure in polycarbonate.

SUMMARY OF THE INVENTION

An object of the present invention is to provide a bracket which assures increase in the adhesive strength between the bracket made of polycarbonate and the base plate made of a synthetic resin, and in addition, increase in the adhesive strength of the bracket for correcting dentition to the tooth and thus can be durable in a lengthy use for correction of dentition.

The present inventor has made intensive studies on the bonding of polycarbonate including physical bonding methods, and as a result, has found that when an adhesive layer is formed on the polycarbonate surface to be bonded and a microwave or ultrasonic wave is irradiated to this adhesive layer, the adhesive strength between the adhesive layer and the polycarbonate is markedly enhanced, and thus completed the present invention.

That is to say, the present invention relates to the bracket for correcting dentition, which comprises the polycarbonate bracket for correcting dentition, the adhesive layer being applied to the bottom surface of the bracket and subjected to irradiation of the microwave or ultrasonic wave, and the plastically deformable photocuring resin layer having adhesivity and bonded to the adhesive layer.

The present invention further relates to the method for producing the bracket for correcting dentition, wherein the adhesive is applied to the bottom surface of the polycarbonate bracket for correcting dentition and is subjected to the irradiation of the microwave or ultrasonic wave after being cured, and subsequently the plastically deformable photocuring synthetic resin layer having adhesivity is bonded to the bracket.

Further the present invention also relates to the method to improve the adhesivity of the polycarbonate, which comprises applying the adhesive to the polycarbonate surface to be bonded and irradiating the ultrasonic wave or the electromagnetic wave of a microwave range to the adhesive after curing thereof.

Figure 1:
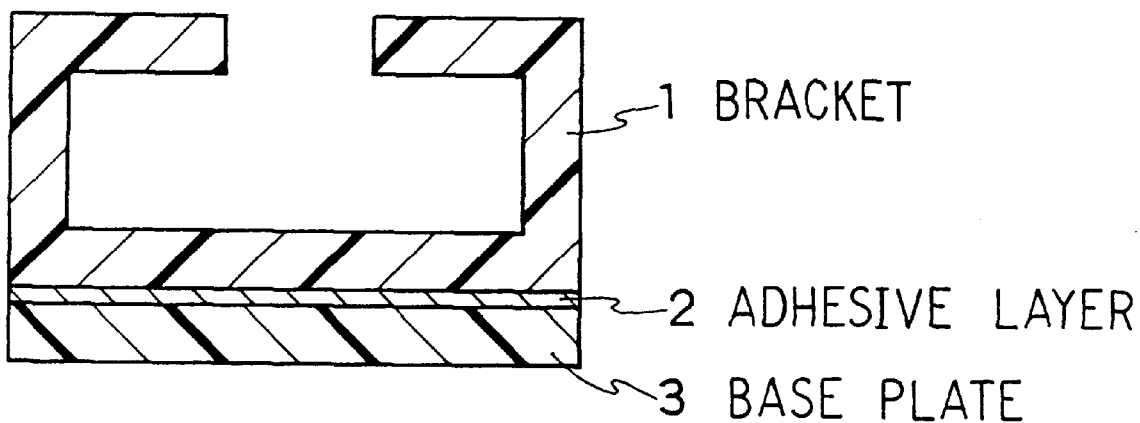
FIG. 1 is an outline sectional view of one example of the bracket for correcting dentition of the present invention.

1 Bracket
2 Adhesive layer
3 Base plate

DETAILED DESCRIPTION

As the methods to improve adhesivity of a synthetic resin such as polycarbonate which is hard to obtain an adhesive strength, there are known various surface modifying methods such as an acidification, flaming, corona discharge treatment, ultraviolet ray irradiation, electron beam irradiation and grafting. However these methods are intended for modification of the synthetic resin surface itself, and are the methods to introduce a polar group such as a carbonyl group into the surface of the synthetic resin. Therefore, the adhesive layer to be applied to the modified surface gives an adhesive strength as it is.

The present invention is the method to improve an adhesivity after the adhesive layer is formed. The adhesive layer formed on the polycarbonate surface and subjected to the irradiation of the microwave or ultrasonic wave has already been cured, and does not function as the adhesive.

Though there is not clarified a reason why an interfacial adhesion between the polycarbonate and the adhesive layer is enhanced by irradiating the microwave or ultrasonic wave onto the adhesive layer formed on the polycarbonate together with the polycarbonate, it is presumed that there occurs any chemical change (bonding) between the polycarbonate and the adhesive.

The bracket for correcting dentition of the present invention comprises the polycarbonate bracket 1, the adhesive layer 2 applied to the bottom surface of the bracket and the plastically deformable photocuring synthetic resin layer 3 (base plate) having an adhesivity as shown in FIG. 1.

As the adhesive forming the adhesive layer, there can be used every known adhesive for various uses, for example, hydroxyethyl methacrylate (HEMA) and triethyleneglycol dimethacrylate, to say nothing of 4-methacryloxyethyltrimellitic anhydride (4META). As described later, an initial adhesive strength of the adhesive layer is not so important. Also as the adhesives, there can be used a photocuring type, chemical polymerization type or so-called cyanoacrylate-based momentary adhesive. As the photocuring type adhesive, there is, for example, CLASPER-F BOND (Trademark, available from Kuraray Co., Ltd.), as the chemical polymerization type adhesive, there are, for example, MCP BOND and ORTHOMITE SUPER BOND (Both are trademarks available from SUN MEDICAL KABUSHIKI KAISHA), and as the cyanoacrylate-based momentary adhesive, there is, for example, ALON ALFA (Trademark, available from ALON KASEI KOGYO KABUSHIMI KAISHA).

The coating amount of the adhesive may be one sufficient for applying it over the whole bottom surface of the bracket, and particularly thick coating is not necessary. The adhesive may be applied to a part of the bottom surface of the bracket, if the adhesive strength to be obtained is in the required range.

The adhesive is once cured after applied. The chemical polymerization type and cyanoacrylate-based adhesives are cured if they are left as applied, but in case of the photocuring type adhesive, it is cured by emitting light thereto. Though a necessity of curing the adhesive once is not clear, it is not preferable if the microwave or ultrasonic wave is emitted without curing the adhesive, since the adhesive undergoes a heat deterioration before curing because of an internal heating caused by that emission.

The microwave or ultrasonic wave is emitted to the adhesive having been cured on the bottom surface of the bracket. The frequency of the microwave to be used is from about 500 to about 3,000 MHz, preferably from about 1,000 to about 2,500 MHz. The emission time is from about 10 to about 300 seconds, preferably from about 30 to about 120 seconds. An atmosphere to be used at the time of the emission is not particularly limited, and the emission can be carried out in air at room temperature. This emission of the microwave can be conducted easily by means of a commercially available electronic oven.

In the emission of the ultrasonic wave, the adhesive may be subjected to the emission of the ultrasonic wave having a frequency of 10 to 50 KHz, preferably 15 to 30 KHz being usually used on an ultrasonic welder for about 1 to about 10 seconds, preferably 2 to 5 seconds with a horn being directed to the adhesive layer. The emission can be carried out in air at room temperature. In order to generate the ultrasonic wave having the above-mentioned range of frequency, for instance, an ultrasonic welder can be used.

In order to further increase the adhesive strength between the adhesive layer and the bracket, the known surface roughening treatment or surface modifying treatment may be conducted previously on the bottom surface of the bracket. As the surface roughening treatment, there are, for example, a sand blasting method and a method using a sand paper. As the surface modifying treatment, there is, for example, the above-mentioned acidification treatment.

The base plate to be bonded to the bracket through the adhesive layer interposed therebetween is not particularly limited if it is a plastically deformable photocuring synthetic resin having adhesivity. This base plate is one for accurately setting the bracket at the desired position of the tooth at the desired angle. The shape of the base plate is taken by pressing it onto the tooth, and the base plate is photo-cured as it is. Then the base plate is fixed to the tooth by means of another adhesive. Of course, the adhesive may be previously coated on the tooth coming into contact with the base plate, and the base plate may be bonded at the same time when pressed onto the tooth.

As the materials of the base plate, there are, for example, thermosetting resins such as epoxy resin, acrylic resin and phenolic resin; UV setting resins such as epoxy resin and acrylic resin; and thermoplastic resins such as polyolefin resin, polyester resin, polyamide resin and polycarbonate resin.

The method to improve the adhesive strength of polycarbonate to be used for producing the bracket for correcting dentition of the present invention can be applied as it is, to the improvement of adhesivity of polycarbonate, and exhibits its power for the adhesion of various polycarbonate products other than the bracket for correcting dentition.

Next, the present invention is explained by means of Example, but is not limited thereto.

EXAMPLE 1

The photocuring type adhesive (CLASPER-F BOND) was applied all over the bottom surface of the bracket for correcting dentition (made of polycarbonate, 3×4×1.7 mm), and light (wave length 470 nm) was emitted to the adhesive for 300 seconds by the use of a halogen lamp (VIDEO LIGHT G-151 available from LPL) to cure it. Subsequently the bracket coated with the adhesive was put in the electronic oven (ER-VE3 available from Toshiba Corporation. A range of microwave used was from 1 to 2 MHz), and the microwave was emitted for 120 seconds.

The base plate (trademark is CLEARFILL PHOTOCORE available from Kuraray Co., Ltd.) was pressed and bonded onto the adhesive layer of the bracket immediately after the bracket is taken out from the electronic oven, and thus the bracket for correcting dentition was produced.

In order to measure the adhesive strength of this bracket for correcting dentition, an aluminum plate was bonded to it. Afterwards light (wave length 470 nm) as emitted for 10 seconds by the use of a visible light emitter (LIGHTEL available from Kuraray Co., Ltd.) to cure the base plate, and thus the bracket for test use was produced. The adhesive strength of this bracket for test use was measured in the manner mentioned hereunder. The results are shown in Table 1. Also for comparison, the adhesive strength in the case where no microwave was emitted was measured.

(Method to measure adhesive strength)

The aluminum plate of the bracket for test use is fixed, and the bracket is pulled in the direction vertical to the aluminum plate. The adhesive strength means a load (Kg) when the base plate is separated from the bracket.

EXAMPLE 2

The bracket for correcting dentition was produced in the same manner as in Example 1 except that as the adhesive, there was used a chemical polymerization type adhesive (MCP BOND), and also the bracket for test use was produced in the same manner as in Example 1. The adhesive strength was measured, and the results thereof are shown in Table 1.

In this Example, since a photocuring type adhesive was not used as the adhesive, a photocuring treatment of the adhesive before the emission of the microwave was omitted.

EXAMPLE 3

The bracket for correcting dentition was produced in the same manner as in Example 2 except that as the adhesive, there was used the cyanoacrylate-based momentary adhesive (ALON ALFA). Also the bracket for test use was produced in the same manner as in Example 2. The adhesive strength was measured and the results thereof are shown in Table 1.

TABLE 1

| | Bracket for correcting dentition | | Adhesive strength (Kg) | |
|---|---|---|---|---|
| Example | Adhesive | Base plate | Microwave emission | No microwave emission |
| 1 | CLASPER-F BOND | CLEARFILL PHOTOCORE | 4.9 | 1.6 |
| 2 | MCP BOND | CLEARFILL PHOTOCORE | 4.4 | 2.3 |
| 3 | ALON ALFA | CLEARFILL PHOTOCORE | 5.3 | 0.7 |

As it is clearly seen from Table 1, the adhesive strength is increased by about 2 to about 8 times by emitting the microwave.

EXAMPLE 4

The photocuring type adhesive (CLASPER-F BOND) was applied all over the bottom surface of the bracket for correcting dentition (made of polycarbonate, 3×4×1.7 mm), and light (wave length 470 nm) was emitted to the adhesive for 300 seconds by the use of a halogen lamp (VIDEO LIGHT G-151) to cure it. Subsequently the cured adhesive layer was subjected to the emission of the ultrasonic wave having a frequency of 20 KHz, an output of 1 kW and an amplitude of 25 $\mu$m for 4 seconds with a horn of an ultrasonic welder (1203B/P48B made by SEIDENSHA DENSHI KOGYO KABUSHIKI KAISHA) being directed to the cured adhesive layer.

The base plate (Trademark CLEARFILL PHOTOCORE. available from Kuraray Co., Ltd.) was pressed and bonded onto the adhesive layer of the bracket immediately after the bracket is taken out from the ultrasonic welder, and thus the bracket for correcting dentition was produced.

In order to measure the adhesive strength of this bracket for correcting dentition, an aluminum plate was bonded to it. Afterwards light (wave length 470 nm) was emitted for 10 seconds by the use of a visible light emitter (LIGHTEL available from Kuraray Co., Ltd.) to cure the base plate, and thus the bracket for test use was produced. The adhesive strength of this bracket for test use was measured in the same manner as in Example 1. The measured strength was increased by about three times as compared with the test use bracket which was not subjected to the emission of light.

EXAMPLE 5

The bracket for correcting dentition was produced in the same manner as in Example 4 except that as the adhesive, there was used the chemical polymerization type adhesive (MCP BOND). Also the bracket for test use was produced in the same manner as in Example 1, and the adhesive strength was measured. The measured strength was about three times that of the bracket which was not subjected to the emission of light.

In this Example, since there was no photocuring type adhesive used, a photocuring treatment of the adhesive before the emission of the ultrasonic wave was omitted.

EXAMPLE 6

The bracket for correcting dentition was produced in the same manner as in Example 5 except that as the adhesive, there was used the cyanoacrylate-based momentary adhesive (ALON ALFA). Also the bracket for test use was produced in the same manner as in Example 5, and the adhesive strength was measured. The measured strength was about five times that of the bracket which was not subjected to the emission of light.

According to the present invention, there can be obtained the polycarbonate bracket of which adhesivity is markedly increased as compared with conventional ones wherein sufficient adhesive strength is hard to obtain.

What we claim is:

1. A method for improving adhesivity of polycarbonate, characterized in that an adhesive is applied to a bond surface of the polycarbonate, and after curing of the adhesive, an electromagnetic wave in the range of a microwave is irradiated to the adhesive layer.

2. A method for improving adhesivity of polycarbonate, characterized in that an adhesive is applied to a bond surface of the polycarbonate, and after curing of the adhesive, an ultrasonic wave is irradiated to the adhesive layer.

* * * * *